(12) United States Patent
Brun

(10) Patent No.: US 6,524,375 B2
(45) Date of Patent: Feb. 25, 2003

(54) VEHICLE CABIN AIR FILTER, A VEHICLE INCLUDING SUCH A FILTER, AND A METHOD OF MANUFACTURE

(75) Inventor: Philippe Brun, Vineuil (FR)

(73) Assignee: Filtrauto, Montigny le Bretonneux (FR)

( * ) Notice: Subject to any disclaimer, the term of this patent is extended or adjusted under 35 U.S.C. 154(b) by 0 days.

(21) Appl. No.: 09/838,413

(22) Filed: Apr. 19, 2001

(65) Prior Publication Data
US 2001/0039882 A1 Nov. 15, 2001

(30) Foreign Application Priority Data
Apr. 21, 2000 (FR) .............................. 00 05176

(51) Int. Cl.$^7$ .............................. B01D 50/00; A61L 9/04
(52) U.S. Cl. ..................... 96/222; 96/223; 55/385.3; 261/DIG. 88; 422/123; 454/158
(58) Field of Search ................. 422/120, 123; 454/158, 156; 55/385.3, 524; 96/222, 223, 226; 261/DIG. 88

(56) References Cited

U.S. PATENT DOCUMENTS

| | | | |
|---|---|---|---|
| 3,017,239 A | * | 1/1962 | Rodman |
| 3,722,182 A | * | 3/1973 | Gilbertson |
| 4,065,262 A | * | 12/1977 | Petroff ........................ 55/279 |
| 4,118,226 A | | 10/1978 | Bourassa ..................... 55/483 |
| 4,514,461 A | * | 4/1985 | Woo ........................... 428/240 |
| 4,604,114 A | | 8/1986 | Ward ........................... 55/501 |
| 4,813,344 A | * | 3/1989 | Greif ........................... 422/124 |
| 5,098,621 A | | 3/1992 | Hermann ..................... 264/46.4 |
| 5,156,843 A | * | 10/1992 | Leong et al. ................. 424/411 |
| 5,273,487 A | | 12/1993 | Dauvergne ................... 454/139 |
| 5,310,548 A | | 5/1994 | Tsuru et al. .................. 424/402 |
| 5,455,048 A | | 10/1995 | Lahmani et al. .............. 424/490 |
| 5,746,231 A | | 5/1998 | Lesser et al. ................. 131/334 |
| 5,780,055 A | | 7/1998 | Habib et al. .................. 424/464 |
| 5,965,091 A | * | 10/1999 | Navarre et al. ............... 422/122 |
| 6,190,437 B1 | * | 2/2001 | Forsyth ......................... 95/90 |

FOREIGN PATENT DOCUMENTS

| | | |
|---|---|---|
| EP | 0 393 723 | 10/1990 |
| GB | 1335 133 | 10/1973 |
| JP | 54098313 | 8/1979 |
| JP | 01299557 A | * 12/1989 |
| WO | WO 90/09813 | 9/1990 |
| WO | WO 9856735 | 12/1998 |

OTHER PUBLICATIONS

Official Search Report from French Patent Office concerning French priority application No. FR 00 05176, Filed Apr. 21, 2000. Report dated Jan. 10, 2001.

* cited by examiner

Primary Examiner—David A. Simmons
Assistant Examiner—Frank M. Lawrence
(74) Attorney, Agent, or Firm—Marshall, Gerstein & Borun

(57) ABSTRACT

A vehicle cabin air filter whose filter material carries microcapsules containing at least one volatile substance, the microcapsules being suitable for diffusing said volatile substance progressively into the air passing through the filter.

8 Claims, 1 Drawing Sheet

VEHICLE CABIN AIR FILTER, A VEHICLE INCLUDING SUCH A FILTER, AND A METHOD OF MANUFACTURE

FIELD OF THE INVENTION

The present invention relates to vehicle cabin air filters, to vehicles including such filters, and to methods of manufacturing such filters.

More particularly, the invention relates to a vehicle cabin air filter comprising a filter material adapted to retain particles in suspension in the air.

OBJECTS AND SUMMARY OF THE INVENTION

An object of the present invention is specifically to improve known filters of this type, so as to enable them to diffuse volatile substances into the vehicle cabin.

To this end, the invention provides an air filter of the kind in question, wherein the filter material carries microcapsules which contain at least one volatile substance and which are adapted to diffuse said volatile substance progressively into the air passing through the filter, wherein the microcapsules are of a diameter lying in the range 0.5 $\mu$m to 20 $\mu$m; and wherein the microcapsules are of a size that is smaller than the maximum size of the pores of the filter material.

By means of these dispositions, it is possible to diffuse substances such as fragrances, antibacterial compounds, substances that neutralize odors or pollutants, mixtures of such substances, etc. into the cabin of the vehicle.

Presenting the volatile substance in the form of microcapsules makes it possible:

to conserve the volatile substance under optimum conditions prior to using the filter;

to use a wide range of volatile substances almost independently of any chemical compatibility with the filter medium, given that the volatile substance is isolated within the walls of the microcapsules prior to being diffused in the air; and to use methods that are relatively easy to implement and of low cost when depositing microcapsules on the filter material, thus leading to a filter of moderate price.

These dispositions also make it possible to avoid significantly increasing the head loss through the air filter.

In preferred embodiments of the air filter of the invention, use can optionally also be made of one or more of the following dispositions:

the microcapsules are distributed over at least a portion of the thickness of the filter material;

the volatile substance contained in the microcapsules contains at least one substance selected from:
  fragrances;
  antibacterial agents; and
  substances suitable for neutralizing gases contained in air;

the volatile substance contained in the microcapsules is selected from substances that are liposoluble and substances that are hydrosoluble;

each microcapsule has a thin outer wall made of a material selected from porous aminoplast polymers, polyamide polymers, polyurethane polymers, and cellulose polymers;

the microcapsules adhere to the filter material by chemical compatibility;

the microcapsules adhere to the filter material by means of a chemical binder; and the binder is selected from polyurethane binders, polyamide binders, silicone binders, acrylic binders, and epoxy binders.

The invention also provides a motor vehicle having at least one filter as defined above to filter the air delivered to the vehicle cabin.

Finally, the invention also provides a method of manufacturing a filter as defined above, in which method the microcapsules are deposited on the filter medium by means of a method selected from:

padding;
coating;
spraying;
bath depletion;
silk-screen printing;
passing the filter material over at least one cylinder turning in a liquid containing microcapsules; and
offset printing.

BRIEF DESCRIPTION OF THE DRAWING

Other characteristics and advantages of the invention will appear from the following description of two embodiments, given as non-limiting examples and with reference to the accompanying drawing.

In the drawing.

MORE DETAILED DESCRIPTION

In the various figures, the same references are used to designate elements that are identical or similar.

Figure 1:
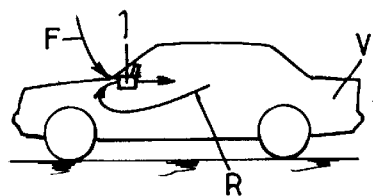
FIG. 1 is a diagrammatic view of a vehicle including a cabin air filter of the invention.

FIG. 1 shows a motor vehicle V fitted with a cabin air filter 1 suitable for filtering:

fresh air F coming from outside the vehicle and subsequently penetrating into the vehicle cabin; and/or recycled air R coming from the vehicle cabin and subsequently returned to the inside of said cabin.

Figure 2:
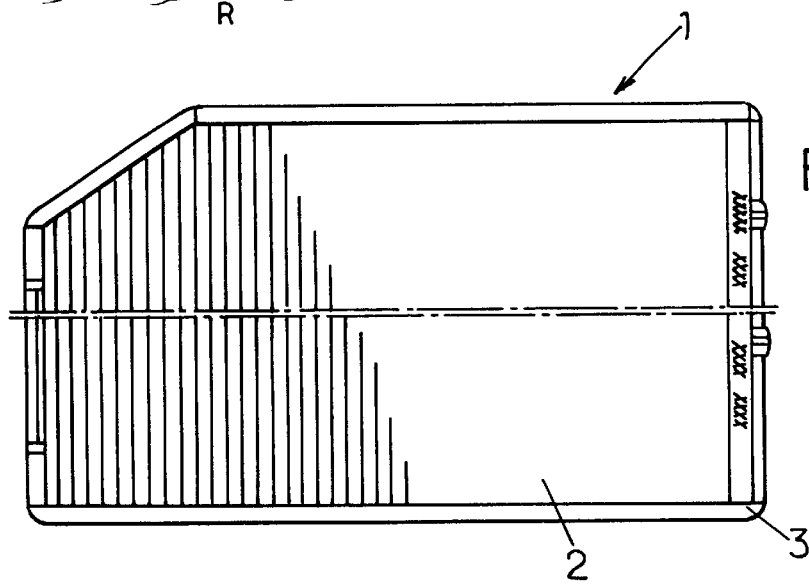
FIG. 2 is a plan view of the cabin air filter belonging to the vehicle of FIG. 1.
Figure 3:
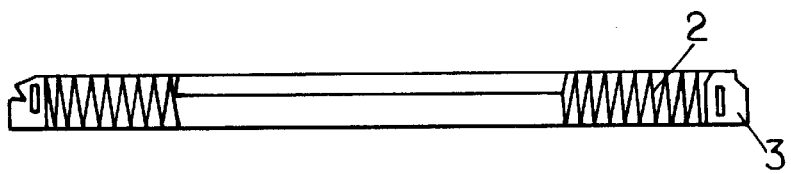
FIG. 3 is a cross-section view of the FIG. 2 air filter.

As shown in FIGS. 2 and 3, the air filter 1 can be in the form of a plate of filter material 2, in particular a material such as paper or the like that is in the form of a folded thin sheet. This plate of filter material generally has a peripheral bead 3 of flexible synthetic material which is adapted to enable the filter to be connected in leakproof manner to a housing (not shown) in which it is received.

Figure 4:
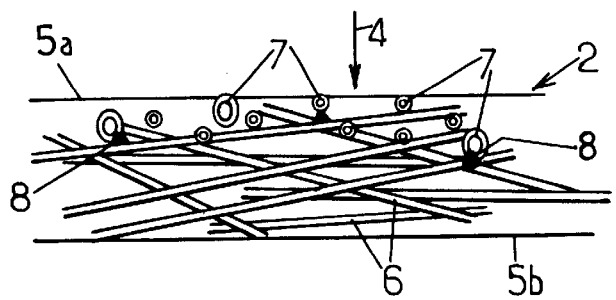
FIG. 4 is an enlarged section view of the sheet of filter material constituting the FIG. 3 filter, in a first embodiment of the invention.

As shown in FIG. 4, the filter material 2 generally has fibers 6 such as cellular fibers or synthetic fibers that are bonded together by chemical or thermal bonds. Microcapsules 7 are placed within these fibers, which microcapsules are suitable for progressively diffusing a volatile substance into the air that passes through the filter throughout the lifetime of the filter (for example over a period of about 6 months). The end of filter lifetime can be determined by the user, in particular by the fact that an odor diffused by the filter is absent, or possibly by the filter diffusing a characteristic odor that is different from its normal odor.

Figure 5:
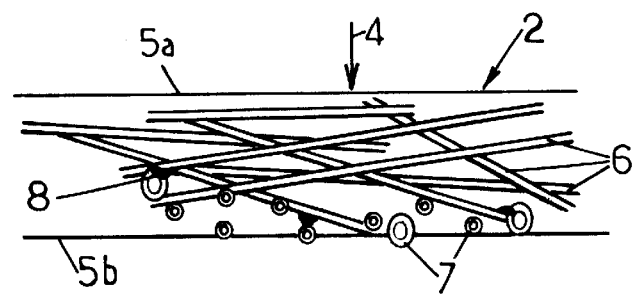
FIG. 5 is a view similar to FIG. 4 showing a second embodiment of the invention.

The microcapsules 7 can be deposited amongst the fibers of the filter material in the vicinity of the upstream face 5a of the filter material 2 relative to the air flow 4 that passes through said material, as shown in FIG. 4. In a variant, the microcapsules can alternatively be placed in the vicinity of the downstream face 5b of the filter material 2, as shown in FIG. 5, or indeed the microcapsules can be placed throughout the thickness of the filter material.

The microcapsules 7 are preferably of a diameter that is less than 28 microns ($\mu$m) and lies for example in the range 0.5 $\mu$m to 20 $\mu$m, said diameter nevertheless possibly being as great as several hundred microns in some cases. Advantageously, the diameter of the microcapsules is smaller than the maximum pore size of the filter material. In any event, the size and the surface density of the microcapsules 7 are selected so as to avoid significantly increasing the head loss of the air filter, which head loss can be about 90 Pascals (Pa) for example under normal conditions of operation of the air filter.

In conventional manner, the microcapsules 7 are made by forming a polymerized wall around droplets or particles of the volatile substance to be diffused in the air. The wall material of the microcapsules is adapted to release the encapsulated volatile substance progressively by diffusion through the porous wall of the microcapsule (where appropriate under the effect of a small amount of pressure, several millibars, due to air passing through the filter), or where appropriate by breaking said wall.

Advantageously, the polymer forming the thin wall of each microcapsule 7 can be made of porous aminoplast, of polyamide, or polyurethane, or where appropriate of a cellulose polymer such as ethyl cellulose or cellulose acetate butyrate.

The volatile substance contained in the microcapsules 7 can be constituted, for example:

by a hydrosoluble fragrance or a liposoluble fragrant oil;

a liposoluble or hydrosoluble antibacterial agent;

a substance that destroys harmful gases that can be carried in the air flow, such as N-butane, toluene, $SO_2$, $NO_2$, formaldehydes, etc.: by way of example, it is possible to use neutralizing substances such as caustic soda for neutralizing acid gases, potassium permanganate for neutralizing formaldehydes, in particular those that come from new plastics, etc.;

a substance adapted to neutralize odorous gases contained in air so as to mask the odor thereof; or a combination of these substances.

The microcapsules 7 can easily be impregnated in the thickness of the filter material 2, in particular by using one of the following techniques:

padding, i.e. pressing the sheet of filter material between two cylinders after depositing the microcapsules by soaking the sheet of filter material in a liquid containing said microcapsules;

coating a paste or similar substance containing the microcapsules which is then spread over the surface of the filter material so as to make said surface uniform;

spraying a liquid containing the microcapsules onto the surface of the filter material;

depleting a bath (ion exchange enabling the microcapsules to be grafted onto the filter material);

silk-screen printing, preferably with drying in a hot air oven;

heliography or the like, i.e. causing smooth or etched cylinders to turn in a bath of liquid containing the microcapsules and allowing the filter material to pass over the cylinder so as to deposit the microcapsules thereon; and offset printing, etc.

Advantageously, the microcapsules can be grafted onto the fibers 6 of the filter material by chemical bonds 8, in particular by means of a polyurethane, polyamide, silicone, acrylic, or epoxy binder. By way of example the binder can be applied to the filter material 2 or to the microcapsules 7 before the microcapsules are deposited on the filter material, the binder than causing the microcapsules to adhere to the filter material merely on making contact therewith, or after heat or other treatment has been applied.

In a variant, the microcapsules can also adhere to the fibers of the filter material merely by chemical compatibility.

In a particular embodiment which has given full satisfaction, microcapsules were made having a diameter lying in the range 4 $\mu$m to 8 $\mu$m, containing a "vine peach" fragrance encapsulated in a thin wall of porous aminoplast. The porous aminoplast represented 4% by weight of the microcapsules. The microcapsules were deposited on filter paper by being sprayed through a checkerboard mask, to a surface density of 20 grams per square meter ($g/m^2$), the microcapsules being bonded to the fibers of the filter material by means of an acrylic resin.

What is claimed is:

1. A motor vehicle comprising a cabin into which a flow of air enters through at least one vehicle cabin air filter comprising a filter material through which said flow of air enters the cabin, said filter material having pores and being adapted for retaining particles in suspension in said flow of air traversing said filter material, wherein the filter material carries microcapsules which contain at least one volatile substance and which are adapted to diffuse said volatile substance progressively into said flow of air, by the effect of pressure due to said flow of air passing through the filter material, wherein the microcapsules are of a diameter lying in the range 0.5 $\mu$m to 20 $\mu$m, and wherein the microcapsules are of a size that is smaller than the maximum size of the pores of the filter material.

2. A vehicle according to claim 1, in which said filter material has a certain thickness and the microcapsules are distributed over at least a portion of the thickness of the filter material.

3. A vehicle according to claim 1, in which the volatile substance contained in the microcapsules contains at least one substance selected from:

fragrances;

antibacterial agents; and substances suitable for neutralizing gases contained in air.

4. A vehicle according to claim 1, in which the volatile substance contained in the microcapsules is selected from substances that are liposoluble and substances that are hydrosoluble.

5. A vehicle according to claim 1, in which each microcapsule has a thin outer wall made of a material selected from porous aminoplast polymers, polyamide polymers, polyurethane polymers, and cellulose polymers.

6. A vehicle according to claim 1, in which the microcapsules adhere to the filter material by chemical compatibility.

7. A vehicle according to claim 1, in which the microcapsules adhere to the filter material by means of a chemical binder.

8. A vehicle according to claim 7, in which the binder is selected from polyurethane binders, polyamide binders, silicone binders, acrylic binders, and epoxy binders.

* * * * *